US00PP08539P

United States Patent [19]

Simpson et al.

[11] Patent Number: Plant 8,539

[45] Date of Patent: Jan. 11, 1994

[54] SPATHIPHYLLUM PLANT NAMED PRESTIGE

[75] Inventors: Donald Simpson, Apopka; Robert D. Hartman, Lake Placid, both of Fla.

[73] Assignee: Twyford International, Inc., Santa Paula, Calif.

[21] Appl. No.: 994,988

[22] Filed: Dec. 22, 1992

[51] Int. Cl.[5] ..... A01H 5/00

[52] U.S. Cl. ..... Plt./88.1

[58] Field of Search ..... Plt. 88.1

*Primary Examiner*—James R. Feyrer

*Attorney, Agent, or Firm*—Foley & Lardner

[57] ABSTRACT

A spathiphyllum plant named Prestige characterized by its dark, shiny and relatively short leaves, short and spreading growth habit, and its sunken veins that are less prominent than the veins of the parent cultivar Lynise.

1 Drawing Sheet

The new cultivar comprises a spathiphyllum sport or mutation discovered by the inventors Donald Simpson and Robert D. Hartman, and is referred to by the cultivar name Prestige. The mutation was discovered growing among plants of the parent cultivar Lynise in Apopka, Fla., and was recognizable by its much shinier leaves than the parent cultivar Lynise. It possesses several other differences as will be described below.1

Asexual propagation of Prestige by division at our production facilities in Palmdale, Fla., was thereafter carried out to increase the number of plants for evaluation and to demonstrate the stability of the combination of characteristics of Prestige from generation to generation. Propagation can also be by way of tissue culture.

The following observations, measurement and values describe plants of Prestige grown in Apopka, Fla. under greenhouse conditions which closel approximate those generally used in horticultural practice.

The following traits have been repeatedly observed to be characteristics of the new cultivar which in combination distinguish Prestige from other spathiphyllum cultivars of the same general type, and particularly from Lynise, to which reference is made.

1. Prestige has darker leaves that are less round, shinier, and shorter than the leaves of Lynise.
2. Prestige has less prominent veins that Lynise.
3. Prestige suckers more than Lynise.
4. Prestige is shorter and spreads more than Lynise.
5. The white spathes are carried by wiry pedicels above the leaves.
6. Except for those differing characteristics, the traits of Prestige are generally similar to the traits of the parent cultivar Lynise.

All color references are measured against The Royal Horticultural Society Colour Chart. Colors are as closely approximate as possible. It will be understood that color depends to some extent on horticultural practices such as light level, temperature and fertilization rate, among others.

The accompanying color photograph comprises a front perspective view of typical plants of Prestige, with three plants in a 10" pot being illustrated. The colors are as close as reasonably possible with illustrations of this type.

Origin: Sport or mutation of Lynise.

Classification: Spathiphyllum hybrid cv Prestige.

Propagation: Asexual propagation either by tissue culture or division.

Plant: In a 10" pot, a plant of Prestige produced by division reaches a mature size of approximately 50 cm. to 70 cm. in height and approximately 75 cm. to 90 cm. in width after approximately 45 weeks under normal and appropriate growing conditions.

Leaves:

*Form.*—The leaf blade is ovate having an aristate, acuminate tip and a more acute base than Lynise. The margins are entire and less wavy than Lynise along the edge. The midrib tends to curve down toward the tip. The leaf blade is medium in thickness and tends to be straight over the width of the leaf. The leaf surface is shiny with a ribbed (though less so than Lynise) appearance.

*Size.*—Leaf blades of a mature size plant are approximately 33 cm. to 40 cm. in length and approximately 12 cm. to 16 cm. in width.

*Petiole.*—The petiole is approximately 40 cm. to 50 cm. in length from the base of the petiole to the base of the leaf blade on the primary shoot. Secondary shoots may be somewhat smaller depending on the age of the shoot. The petiole is approximately 4 mm. to 6 mm. in diameter just below the geniculum. The petiole curves at the geniculum.

*Petiole wings.*—Petiole wings are approximately 25 cm. to 35 cm. in length and approximately 6 mm. to 10 mm. in width at its midpoint. The tip of the petiole wings is aristate. There is approximately 10 cm. to 15 cm. between the top of the wing and the base of the leaf.

*Geniculum.*—The geniculum is approximately 42 mm. to 47 mm. in length and approximately 6 mm. to 10 mm. in diameter. The color is more yellow than 137C. The geniculum is curved and prominent. There is no space between the top of the geniculum and the base of the leaf blade.

*Veins.*—Veins are sunken, though less so than Lynise, with the leaf blade slightly rounded (more so than Lynise) between veins on the upper surface. Veins protrude, though less so than Lynise, on the lower surface side. There are approximately 20 to 24 primary veins on the leaf.

*Color.*—Mature leaf: Upper surface: 137A. Lower surface: Greyer than 137C, greener than 191A. Upper surface of midrib: 137A. Lower surface of midrib: Lighter than 144C. Petiole: 137A, B. Petiole wing: 137A, B.

Inflorescence:

*Immature.*—The spathe is tightly rolled around the spadix and extrudes from the petiole sheath. The spathe is fully open approximately when the pedicel is fully elongated—approximately 60 cm. to 80 cm. above the soil surface.

*Spathe.*—Color: Fully open: Front: 155D. Back: 155D. Faded: Front: 138B. Back: 138B. Arrangement: The spathe stands up on straight wiry pedicels and opens vertically above the leaves. Shape: The spathe is oval with an aristate apice that is straight. The base of obtuse. The spathe is slightly cupped when first open and is approximately 20 cm. to 28 cm. in height and approximately 9 cm. to 12 cm. in width. It is approximately 1 cm. to 2 cm. in depth. Flowering time: After approximately 40 to 50 weeks for an untreated plant depending on season, approximately 1 to 3 blossoms will be present. Smaller blossoms may occur on less mature growth.

Reproductive organs:

*Spadix.*—Size: Approximately 7 cm. to 10 cm. in height and approximately 18 cm. to 25 mm. in width. Color: When the spathe unrolls, the spadix is 158C gradually changing to 147A before senescing.

*Stamens.*—Anthers and filaments are not clearly visible.

*Pollen.*—White in color.

*Pistil.*—158C in color, protruding between the staminate flowers, firmly fixed to the main axil. The pistilate flowers extend approximately 2 mm. to 4 mm. beyond the staminate flowers.

Roots: White fleshy roots with fine laterals.

I claim:

1. A new and distinct cultivar of spathiphyllum plant named Prestige, as illustrated and described.

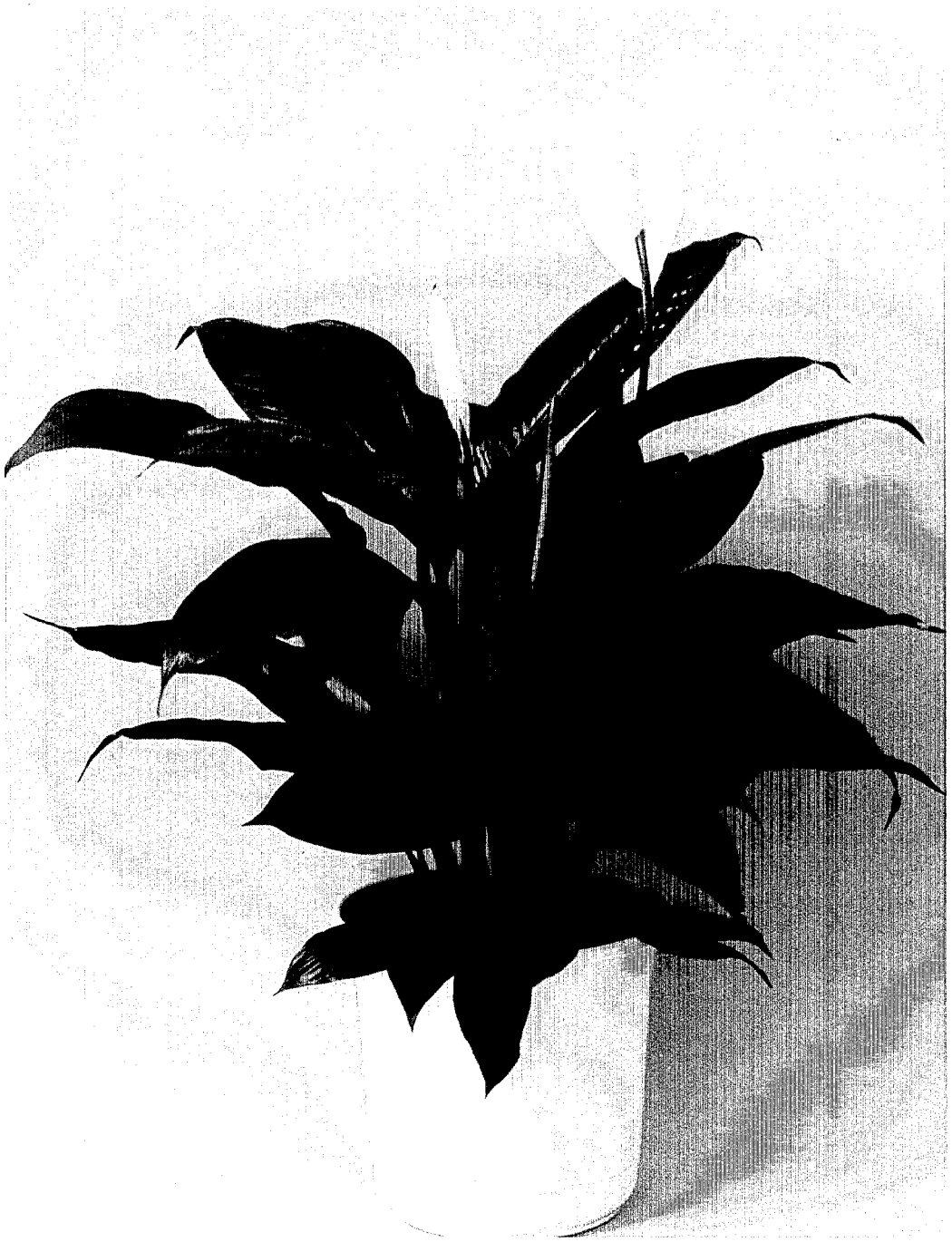

* * * * *